United States Patent [19]
Sick

[11] Patent Number: 4,671,663
[45] Date of Patent: Jun. 9, 1987

[54] OPTICAL FAULT SEEKING APPARATUS

[75] Inventor: Erwin Sick, Icking, Fed. Rep. of Germany

[73] Assignee: Erwin Sick GmbH Optik-Elektronik, Fed. Rep. of Germany

[21] Appl. No.: 811,099

[22] Filed: Dec. 19, 1985

[30] Foreign Application Priority Data

Dec. 19, 1984 [DE] Fed. Rep. of Germany ....... 3446355

[51] Int. Cl.[4] ............................................ G01N 21/84
[52] U.S. Cl. .................................... 356/430; 356/431;
356/238
[58] Field of Search ....................... 356/430, 431, 238;
280/562, 563; 250/572

[56] References Cited

U.S. PATENT DOCUMENTS

| 3,430,055 | 2/1969 | Metzger | 250/572 |
| 3,797,943 | 3/1974 | Nagao et al. | 356/431 |
| 4,110,047 | 8/1978 | Takahashi | 250/572 |

FOREIGN PATENT DOCUMENTS

| 2423340 | 11/1974 | Fed. Rep. of Germany . |
| 2404972 | 8/1975 | Fed. Rep. of Germany . |
| 2727926 | 1/1979 | Fed. Rep. of Germany . |

OTHER PUBLICATIONS

The brochure, "Mit dem Sick Scan System die Qualitat steigern".

*Primary Examiner*—R. A. Rosenberger
*Assistant Examiner*—Crystal D. Cooper

[57] ABSTRACT

Figure 1:
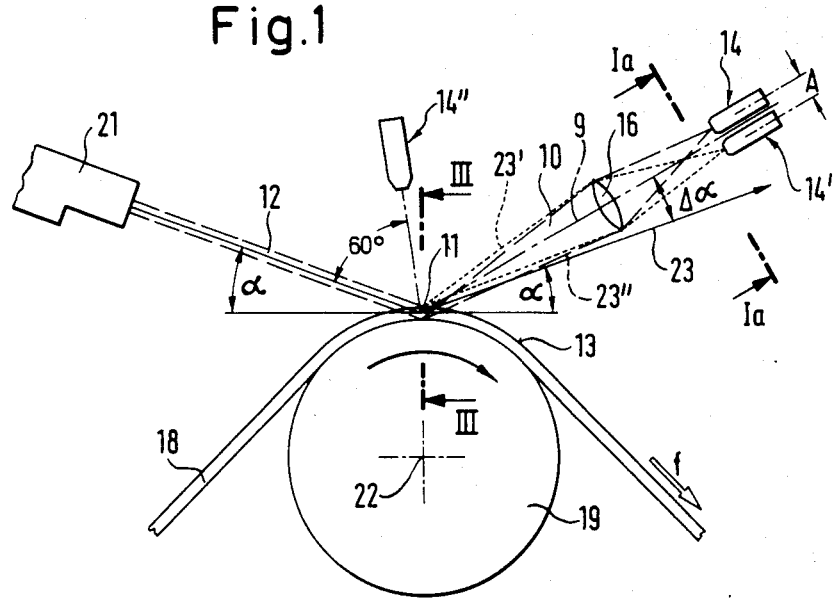

An optical fault seeking apparatus has a light scanning apparatus (21) and a light line receiving apparatus (14) which receive the light reflected from the material to be investigated and direct it onto a photoelectric converter. The light beam which forms the light line 11 impinges at an acute angle ($\alpha$) onto the surface (13) of the article or web (18) under investigation. The image forming optical light line receiving apparatus (14), effectively consists of two light receivers (14, 14') positioned away from the normally reflected beam (23) and arranged to receive light from respective ones of two spaced apart strip-like regions (11', 11'') extending parallel to and partly overlapping the line of light (11). In this way the device is able to detect faults (e.g. lumps or depressions) in fleece-type webs with irregular surface structures which are normally very difficult to monitor with optical fault seeking apparatus (FIG. 1).

25 Claims, 13 Drawing Figures

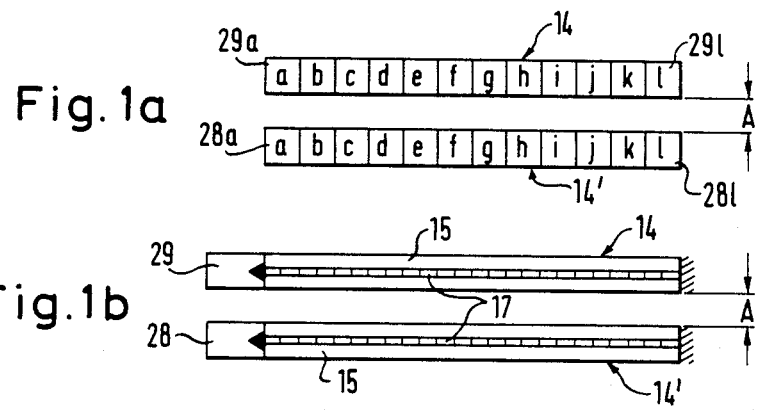
Fig.1a
Fig.1b
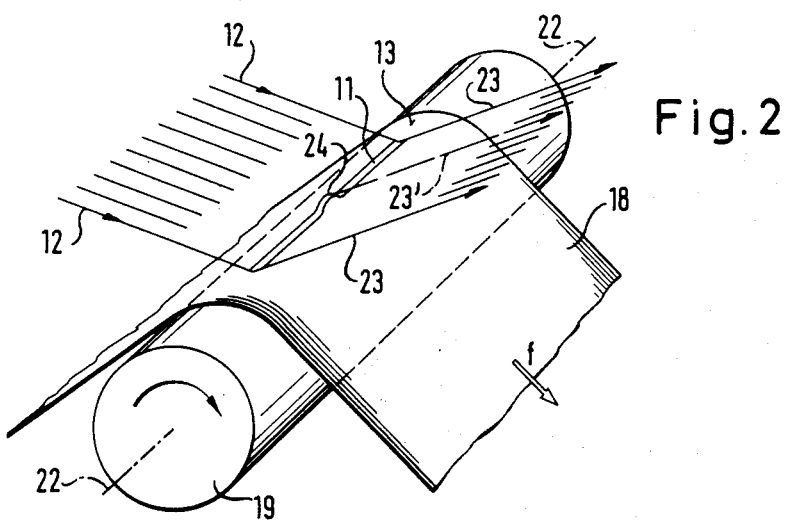
Fig.2

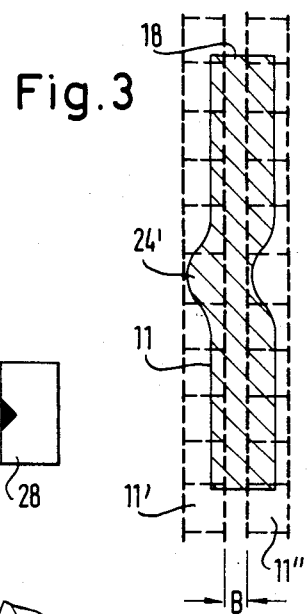
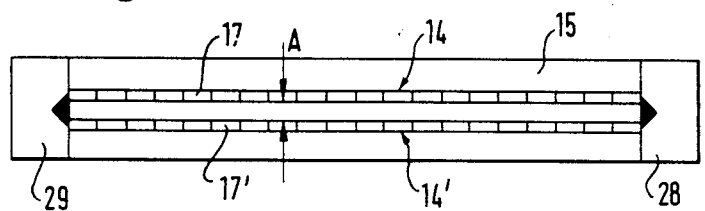
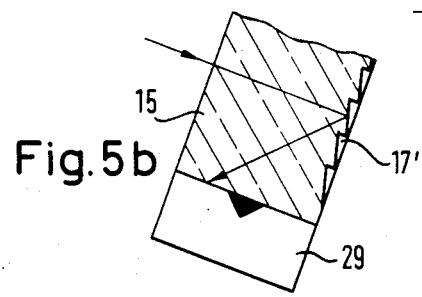
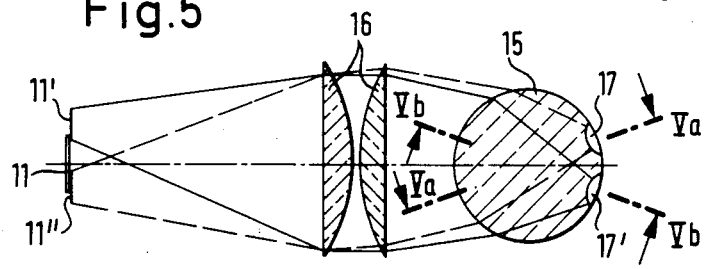
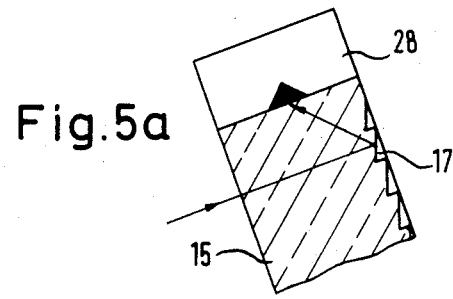

OPTICAL FAULT SEEKING APPARATUS

The invention relates to an optical fault seeking apparatus comprising:

a light scanning device which generates a strip-like line of light on the material web to be investigated which consists in particular of transluscent material such as fleece material (non-woven material), which is convexly curved, in particular by leading it partly around a roller, and which is preferably continuously moved in its longitudinal direction, wherein the strip-like line of light extends with fault-free material transverse to the longitudinal direction over the web expediently at the apex of the curvature;

and a light receiving device which contains photoelectric converters onto which the light emerging from the line of light on the illuminated material is deflected, and wherein the light which generates the line of light impinges at a shallow angle onto the material.

An apparatus for finding faulty points of a band is known (German Offenlegungsschrift No. DE-OS 14 73 743), in which a line of photodiodes is arranged relatively close to the line of light generated by a light source via a condensor and a cylinder lens, with the line of photodiodes receiving the light normally reflected from the line of light. If dust or other contaminations are present on the material web on which the line of light is generated, then the diode line receives less light at the relevant position, which can be exploited to generate a fault signal.

An apparatus of this kind is however not suited for fault seeking with spun fleeces or non-woven felt-like webs. A spun fleece or a non-woven felt-like material web can namely have various thicknesses and compositions. All constructions with intermediate thicknesses are possible from the thinnest gossamer-like layers up to thick fleece-like webs of paper, synthetic fibres, cellulose or also glass fibres. The pronounced irregular structure is however common to all such felt-like material webs.

This irregular structure of such felt-like fabrics, which is irregular from the very outset makes optical fault seeking difficult, because even fault-free material has a high background noise. This background noise impairs to a high degree the discovery of individual faults during surface inspection of a customary nature, for example by transmission measurement or by judging the change of the reflected light due to errors in the material. Much the commonest faults are thickened portions, threads lying on the surface and/or accumulations of adhesive.

German Offenlegungsschrift No. 1473742 discloses an apparatus for finding faulty locations which are too thick in a layer consisting of a viscous fluid applied to the surface of a strip. The viscous treatment fluid is applied as a layer by means of a nozzle aligned with the strip which is led along a track. The track is arranged so that it is curved and a light source is provided to generate a light beam on the surface of the liquid layer located in the curved track. A light sensitive detector is located between the light beam reflected by a layer of the correct thickness and the track of the strip and receives no light when the condition of the surface is fault-free. If faulty locations arise which are too thin then the reflected beam is displaced in the direction towards the photoreceiver whereby an alarm signal can be initiated. This known apparatus is however only suitable for monitoring relatively narrow track regions and is in particular unsuited to the monitoring of spun fleeces or non-woven felt-like material webs because, if used for this application, it would initiate a fault signal at the incorrect time, and because it is also incapable of showing both elevated regions and also depressions in the material web.

The object underlying the present invention is thus to provide a simply constructed fault seeking apparatus of the initially named kind which, while operating in a reliable manner, is particularly suited to deliver problem-free fault indications even with felt-like material webs which, from their very nature, consist of a very irregular material.

In order to satisfy this object the invention provides that the light receiving device is formed by two light line receivers which respectively have at least one photoreceiver and which are arranged somewhat outside of the angle of regular reflection, and preferably at a somewhat steeper angle, in the light remitted from the material web, parallel to the light line, and at a distance A from one another, such that the light line receiving device detects a strip-like region close to the roller and the other light line receiving device detects a strip-like region removed from the roller, with the two strip like regions being displaced in parallel relative to the strip-like light line, perpendicular to its longitudinal extent, by a predetermined amount B in opposite directions.

The invention operates primarily with an optical scanner as the light scanning device, with the optical scanner having a mirror wheel, a concave mirror and means for focussing the light beam. The scanner generates a continuous sequence of light lines which preferably impinge as a parallel light curtain onto the material which is being guided in a straight line in its longitudinal direction.

It is particularly preferable if the electrical signals which originate from the differential photoreceivers of the two light line receiving devices are connected to an electronic evaluation circuit via a differential amplifier.

In accordance with the invention provision should in particular be made for the light line to be sufficiently wide that it embraces the preferably transluscent material web at least approximately up to the highest raised bump which occurs in practice, and indeed in particular starting from the surface of the roller.

Furthermore, it is expedient if a cylindrical lens arranged in the remitted light beam parallel to the light line images the two strip-like regions onto the two light line receiving devices respectively.

The thought underlying the invention is thus to be seen in that the light remitted from the web near to the normal reflection angle is received by two light line receiving devices arranged at a defined spacing perpendicular to the direction of the light beam and parallel to the line of light. In this way the region of the web close to the roller is imaged onto the one light line receiving device and the region of the web removed from the roller is imaged onto the other light line receiving device. An intermediate region at the centre of the web falls between the two light line receiving devices so that the light leaving this region does not have any influence on the measurement. If the web surface moves away from the roller as a result of a lump, bump or curved region in the vicinity of the incident light beam then the corresponding image developed by the cylindrical lens is displaced onto the associated light line receiving device. The change in the signal which is produced by this at the output of the associated photoreceiver is then a measure for the arching of the web, or the presence of the lump or bump, at the relevant location.

If a depression is present, for example in the region near to the roller, a corresponding displacement of the image formed by the cylindrical lens occurs onto the other light line receiving device.

As a result of the described difference measurement a particularly sensitive indication of thickness changes of the web at points on which the light beam falls can be achieved.

It is particularly preferred if the two strip-like regions are only displaced in opposite directions relative to the light line by such an amount that they still clearly overlap the latter. In particular, the construction should be such that the strip-like regions overlap approximately one half the width of the light line.

A first practical embodiment which in particular enables a spatial differentiation between faults which occur over the transverse extent of the web, is characterised in that the light line receiving devices consist of spaced apart rows of diodes.

However, as the statement that a fault is located at a particular point along the length of the web is generally sufficient a simplified embodiment is also provided which is characterised in that the light line receiving devices each comprise a light conducting rod with a mirror raster at the side surface directly opposite to the incident light, with a photoreceiver being arranged at at least one end face of each light conducting rod. The light conducting rod is in this arrangement in particular constructed in accordance with German Pat. No. DE-PS 21 67 026. I.e. the light which emerges from the light line is received by a cylindrical lens and is projected onto the mirror raster of the light conducting rod. The mirror raster deflects the light sideways and it is conducted by total internal reflection in the interior of the rod to one end of the rod, where the photoreceiver is secured and converts the received light into an electrical signal. Photoelectric converters can be provided at both end faces of the light conducting rod. It is, however, preferable if a photoreceiver, in particular a photomultiplier, is provided at only one end face, while the opposite end face should be made specularly reflecting.

A further embodiment is characterised in that the light line receiving devices are formed by two strip-like mirror rasters of a unitary light conducting rod which are spaced apart by a distance A and which are provided on the side surface of the light conducting rod substantially diametrically opposite to the incident light, with the one mirror raster reflecting the incident light in the direction towards the photoreceiver provided at the one end face at angles of total internal reflection, and with the second mirror raster reflecting the incident light in the opposite direction to the other photoreceiver at angles of total internal reflection. In this embodiment use is made of the possibility of providing two mirror rasters which are peripherally spaced apart from one another on one light conducting rod which is preferably of circular cross-section, with the two mirror rasters deflecting the incident light in opposite directions of the light conducting rod to photoreceivers provided at the opposite ends thereof. In this way one can make do with a single light conducting rod and, in other respects, also provide an indication of relatively minor displacements of the light line in the one or other direction.

Furthermore, it is expedient, if the strip-like regions are sufficiently wide that, on the occurrence of web faults the then deformed light line still largely falls on one of the two strip-like regions.

When using light conducting rods of circular cross-section account should be taken in the design of the image forming cylinder lens of the fact that the circular light conducting rod also has a refractive power similar to that of a cylindrical lens, so that the refractive power of the cylindrical lens arranged in front of it should be selected to be correspondingly smaller. The combined refractive power of the cylindrical lens and of the light conducting rod must be such that the strip-like regions are imaged onto the associated mirror raster.

This special choice of the refractive power of the cylindrical lens is also important in a further advantageous embodiment, which is characterised in that the cylindrical lens forms an image of the two strip-like regions on the two surfaces of a roof-like strip mirror which extends parallel to the light line, with further cylindrical lenses being arranged at 90° to the optical axis and concentrating the images of the strip-like regions on the roof edge mirror onto the mirror rasters of light conducting rods arranged behind them.

In a modification of this embodiment a mirror for deflecting light outwardly is arranged on one side of the optical axis of the cylindrical lens, with the one strip-like region being imaged onto the outwardly deflecting mirror, and with the light of the strip-like region being concentrated via a cylindrical lens arranged at 90° to the optical axis onto a light conducting rod and onto a mirror raster arranged on the latter. In this case the second strip-like region is imaged alongside the outwardly deflecting mirror and is concentrated via a further cylindrical lens and a preferably right-cylindrical light conducting rod onto the mirror raster of the last said light conducting rod.

In accordance with a further preferred embodiment the material web is led around a roller, which is preferably matt black, for vibration-free and fault-free guidance in the scanning line.

A particularly sensitive practical embodiment which nevertheless does not give rise to erroneous fault indications is so constructed that the acute angle of incidence to the surface, i.e. the shallow angle, amounts to from 10° to 30° and in particular to approximately 20°.

In order to obtain a pronouncement concerning the light scattered outside of the normal angle of reflection using the same apparatus, a particularly advantageous further development of the invention provides that a further light line receiving device is provided in the back scattered region, preferably at an angular spacing of from 50° to 70° and in particular approximately 60° relative to the incoming light.

The definition of the strip-like regions of the invention can take place in a particularly simple manner, if the image of the strip-like regions which are displaced to the sides of the light line is brought about by a strip-like aperture diaphragm which is so arranged at the position of an intermediate image formed by the cylindrical lens that only the strip-like regions are received by the light line receiving devices.

This embodiment offers the advantageous possibility of making the strip-like aperture diaphragm adjustable perpendicular to the line of light and to the optical axis, and/or of adjustable width, for matching to the type of material and the sensitivity of the system.

Figure 1C:
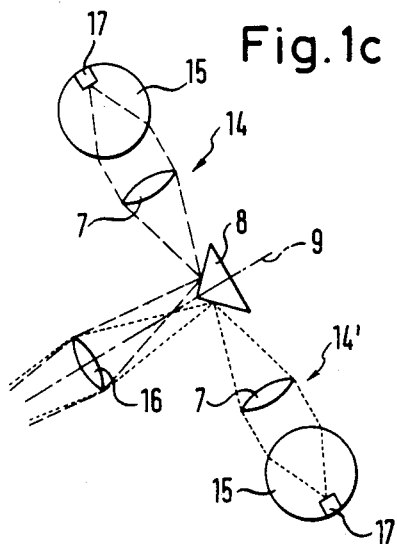
Figure 1D:
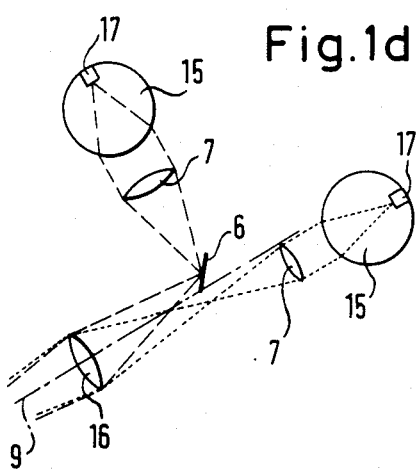
Figure 6:
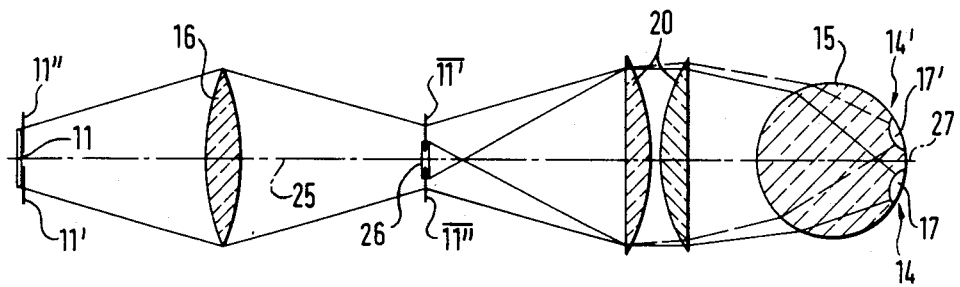
Figure 7:
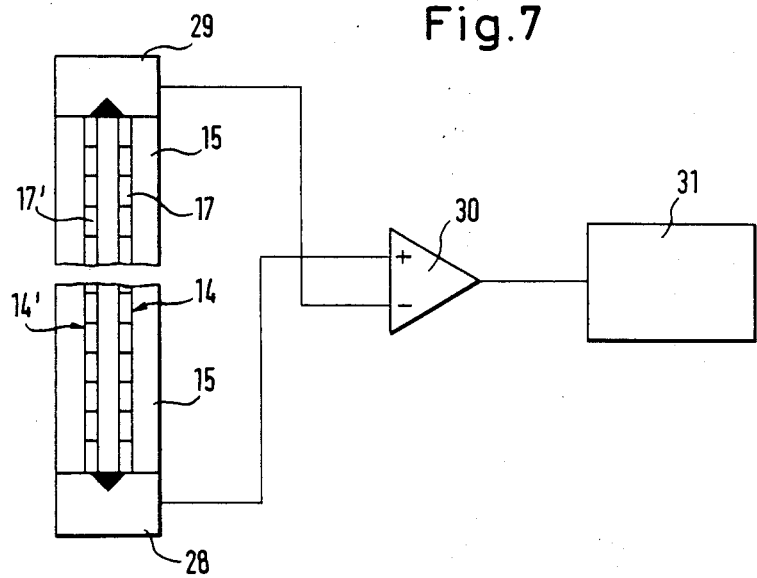

The invention will now be described in the following by way of example and with reference to the drawings which show:

FIG. 1 a schematic side view of an optical fault seeking apparatus in accordance with the invention, FIG. 1a a schematic view on the line Ia—Ia in FIG. 1, FIG. 1b a view analogous to FIG. 1a of an embodiment operating with two light conducting rods, FIG. 1c a section of a side view analogous to FIG. 1 of a further embodiment of the light receiving apparatus of the invention, FIG. 1d a modification of the embodiment of FIG. 1c, FIG. 2 a schematic perspective view of a part of the fault seeking apparatus of FIG. 1 seen obliquely from above, FIG. 3 a sectional view of the web on the line III—III in FIG. 1 to illustrate the light line formed by the illuminating system and the imaged regions 11', 11'', FIG. 4 a view analogous to FIGS. 1a, 1b of a further embodiment which operates with only one light conducting rod but with two mirror rasters, FIG. 5 a side view of the embodiment of FIG. 4 in the direction of the axis of the light conducting rod, FIG. 5a a section on the line Va—Va in FIG. 5, FIG. 5b a section on the line Vb—Vb in FIG. 5, FIG. 6 a section of a further embodiment of an optical fault seeking apparatus in accordance with the invention in which one operates with an intermediate image of the light line, and FIG. 7 a schematic block circuit diagram of an optical fault seeking apparatus in accordance with the invention starting from the embodiment of FIGS. 4, 5.

As seen in FIG. 1 a light scanning device 21 which operates with a laser generates a scanning beam 12 which is displaced parallel to itself and which is incident on the surface 13 of a material web 18 guided partly around a rotating roller 19. The scanning beam 12 is incident on the web at a position where the web is reliably and well guided in a clearly convexly curved form on the surface of the roller 19. The scanning beam 12 executes a periodic scanning movement in the direction of the roller axis 22, i.e. perpendicular to the transport direction f of the material web 18, so that, in accordance with FIG. 2, a light line 11 of a predetermined width is generated on the material web 18 and extends transversely to its longitudinal extent. Of course the line of light is not really a line but instead a row of successively illuminated points which resemble a line. It would of course also be possible to illuminate a whole line of the surface at once with a suitable illuminating system.

The angle of incidence $\alpha$ of the scanning beam 12 on the surface of the material 18 amounts, as seen in FIGS. 1 and 2, to 20°. The material web 18 is translucent and light scattering so that it also directs a scattered beam of light 10 outside of the angle of normal reflection 23, for example to a cylindrical lens 16 arranged alongside the normal direction of specular reflection.

At the angle of normal light reflection there emerges, on the assumption of a specularly reflecting material, a reflected light beam 23 which, as seen in FIG. 1, passes beneath two light line receiving devices 14, 14' arranged spaced apart by a distance A. The two light line receiving devices 14, 14' are thus located fractionally above the normally reflected light beam 23. A cylindrical lens 16 extending perpendicular to the plane of the drawing images the point of impingement of the scanning beam 12 on the material web 18 onto the two light line receiving devices 14, 14' in the illustrated manner. The optical axis or better the optical plane 9 of the cylindrical lens 16 has an angle $\Delta\alpha$ of approximately 5° (from 3° to 7° or from 4° to 6°) relative to the direction of the specularly reflected beam 23. In accordance with the invention it is important that the angle $\Delta\alpha$ is added to the angle of reflection $\alpha$, i.e. that the optical axis 9 lies at a steeper angle to the surface of the material web 18 than the imaginary normally reflected ray 23.

As seen in FIG. 1a the light line receiving devices 14, 14' consist of two diode rows arranged parallel to one another and spaced apart by the distance A, with the two diode rows consisting of individual photodiodes 28a to 28l and 29a to 29l respectively. The longitudinal direction of the diode rows is perpendicular to the normally reflected beam 23 and parallel to the light line 11 generated on the material web.

As a result of the arrangement of the invention the region of the material web 18 near to the roller, in the vicinity of the point of incidence of the scanning beam 12, is imaged onto the light line receiving device 14 in the manner illustrated in broken lines, while the region of the material web removed from the roller is imaged by the cylindrical lens 16 onto the lower light line receiving device 14'.

FIG. 1b shows two light line receiving devices 14, 14' which are constructed as light conducting rods and which have a mirror raster 17 at their side surfaces opposite to the light inlet, with the mirror rasters reflecting the light concentrated thereon into the light conducting rod 15 at angles of total internal reflection so that it can reach photoreceivers 28, 29 provided at respective end faces of the light conducting rods. The end faces of the light conducting rods 15 opposite to the photoreceivers can be made specularly reflecting in the manner indicated in FIG. 1b.

Should the distance A be so small that the two light conducting rods 15 cannot be arranged close enough together, then the use of a strip-like ridge mirror 8 in accordance with FIG. 1c is recommended, with the strip-like ridge mirror 8 being arranged on the optical axis 9 of the cylindrical lens 16 and with the surface of the material web 18 being imaged onto the strip-like ridge mirror 8. The light which is reflected through 90° is concentrated via further cylindrical lenses 7 onto two light conducting rods 15 which are constructed as shown in FIG. 1b.

As seen in FIG. 1d it is also possible to use a strip mirror 6 in place of the strip-like ridge mirror 8, with the strip mirror 6 also extending perpendicular to the plane of the drawing at an angle of 45° to the optical axis 9. In this case only the region of the material web 18 close to the roller is imaged onto the strip-like mirror 6. The light which is reflected at 90° is then again concentrated via a cylindrical lens 7 onto the mirror raster 17 of a light conducting rod 15 arranged above it.

The regions of the material web 18 remote from the roller are imaged beneath the strip-like mirror 6 and the light leaving this image is concentrated by a cylindrical lens 7' and a light conducting rod 15' onto a mirror raster 17' arranged on the light conducting rod 15'. The cylindrical lens 7' and the light conducting rod 15' are arranged somewhat below the optical axis 9.

FIGS. 2 and 3 show how the light line 11 is deformed on the presence of a raised fault 24 on the surface 13 of the material web. As this raised fault 24 is illuminated before reaching the zenith of its movement around the roller 19 the light which falls into this region is reflected earlier, and ultimately from a position further from the roller than the light scattered at fault-free positions of the material web surface. The light beam 23' is thus increasingly concentrated through the fault 24 onto the lower light line or light strip receiving device 14'. Vice-versa, a depression in the web surface would lead to a displacement of the reflected light beam in the upper direction so that the light now moves up from the light line to the light line receiving device 14.

If a raised arch 14 of the web is associated with a corresponding depression in the region of the web near to the roller, as indicated in FIG. 3, then the light beam 23" remitted from the region of the web near to the roller is also increasingly concentrated on the upper light line receiving device 14.

As can be seen from FIG. 3 the cylindrical lens 16 thus forms an image of the two strip-like regions 11', 11" onto the light line receiving devices 14, 14' which are spaced apart by a distance B and are just sufficiently wide that they each detect part of the light line 11.

Important for this effect is the fact that the light beam 12 impinges at a relatively acute angle of approximately 20° or slightly less onto the surface so that the bulging of the light line 11 due to a faulty location 24 is as pronounced as possible. The guidance of the material web 18 around the curved peripheral surface of the roller 19 also contributes in advantageous manner to the generation of a pronounced bulging of the light line 11 at fault location 24.

As seen in FIG. 1 a further light line or light strip receiving device 14" is also arranged at an angle of 60° relative to the incident light beam 12 and is able to receive and to measure light which is back scattered from the material web at the relevant angle, in order, in this manner, to obtain additional information concerning the light scattering characteristics of the material web.

FIG. 3 illustrates the image forming characteristics which the fault seeking apparatus of the invention should have relative to the light line 11. FIGS. 3 shows the comparatively broad light line 11 which corresponds to the thickness of the material web, with the light line 11 having a bulge 24' at the location of a raised fault 24 (FIG. 2). Two strip-like regions 11', 11" are imaged onto the light strip receiving devices 14, 14' respectively, with these regions having a spacing B and being displaced in parallel relative to the light line 11 in opposite directions. The width of each strip-like region 11', 11" is substantially the same as the width of the light line 11 whereas the sideways displacement is such that each of the strip-like regions 11', 11" still clearly overlaps the light line 11. The regions 11', 11" are disposed close to the roller (11''') and removed from the roller (11') respectively and are sufficiently wide that the changes in thickness brought about by material faults occur in these regions. The regions 11', 11" can be fully illuminated by the scanning beam 12. The width of the light line 11 corresponds to the thickness of the material web.

The photoreceivers 28, 29 associated with the two light strip receiving devices 14, 14' are connected in accordance with FIG. 7, to a differential amplifier 30 which feeds an electronic evaluation circuit 31.

The two strip-like regions 11', 11" are normally displaced in opposite directions relative to the light line 11 in such a way that the two electrical signals generated by the photoreceivers 28, 29 are the same at the input of the differential amplifier 30 so that the signal zero exists at the output of the differential amplifier 30.

If however an upwardly arched defect 24' occurs as indicated in FIG. 3 then the photoreceiver 28 receives more light at the relevant position than the photoreceiver 29 and an imbalance occurs at the input of the differential amplifier 30, which results in a fault signal at the output of the differential amplifier 30, and this fault signal can be evaluated in the electronic evaluation circuit 31.

If, in accordance with FIG. 1a, a diode row is used then each photodiode pair 28a, 29a; 28b, 29b etc. could be connected to a respective differential amplifier so that an individual fault evaluation across the width of the web is possible.

In general however, it is sufficient if one merely shows that a fault is present at a particular point along the web somewhat across the width of the web. In this case two light conducting rods 15 which are arranged parallel to one another spaced apart by the distance A are used Ias the light strip receiving devices 14, 14'. These light conducting rods are provided, as can be seen from FIG. 1b, with a mirror raster 17 at the side diametrically opposite to the light inlet. The mirror rasters, consisting of stepped arrangements of inclined mirrors, direct the incident light at angles of total internal reflection to the respective photoreceivers 28 and 29 arranged at the respective end faces of the light conducting rods. The opposite end faces of the light conducting rods can be made specularly reflecting. The imaging conditions are in this case such that the light originating from the strip-like regions 11', 11" is concentrated onto the mirror rasters 17 of the two light conducting rods 15. Further imaging possibilities are shown by FIGS. 1c and 1d described above.

In accordance with FIGS. 4, 5, 5a and 5b two mirror rasters 17 can also be provided spaced apart by a distance A at the side of a single light conducting rod 15 substantially diametrically opposite to the light inlet. In FIG. 5 the light line 11 and the strip-like regions 11', 11" are schematically illustrated and are imaged via a cylindrical lens 16 and a light conducting rod 15 of right cylindrical shape onto the two strip-like mirror rasters 17 and 17' respectively.

As seen in FIG. 5a the light impinging on the lower mirror raster 17 is deflected by a suitable inclination of the mirror surfaces of the mirror raster 17 onto which the light falls in the direction towards a photoreceiver 28 provided at one end face. In FIG. 5a the reflected light beam falls directly on the photoreceiver 28. If however the scanning beam is at the other end of the material web then the reflected light may first reach the photoreceiver 28 after undergoing total internal reflection one or more times at the surface of the light conducting rod.

The light impinging on the mirror raster 17' is directed in the opposite direction, as a result of the oppositely directed saw-tooth arrangement of the mirror raster 17' onto the photoreceiver 29. In this way it is possible with a single light conducting rod 15 to deflect two light beams coming from different points of the material web to different photoreceivers 28 and 29 respectively.

FIG. 6 shows a similar embodiment in which however an intermediate image of the light line 11 is first formed by the cylindrical lens 16 at the position of an aperture diaphragm 26 which is displaceable transverse to the optical axis 27. The aperture diaphragm 26 covers over the intermediate image, apart from the marginal zones 11' and 11" which are to be used for the evaluations, so that only these marginal zones are imaged onto the mirror raster 17 and 17' of the light conducting rod 15. The marginal zones 11' and 11" are intermediate images of the strip-like regions 11' and 11" on the material web.

By displacement of the aperture diaphragm perpendicular to the optical axis 25 is possible to effect an adjustment of the zero point of the output of the differential amplifier 30, while a suitable choice of the width of the aperture diaphram 26 makes it possible to influence the width of the strip-like regions 11' and 11" that are imaged on the receivers.

In accordance with the invention the spacing A of the light strip receiving devices 14, 14' is selected such that the light deflections and light displacements emerging from the normal structure of the monitored material do not yet change the equilibrium at the differential amplifier 30, but only such raised portions or depressions on the material web which are characteristic of a fault. The invention thus makes it possible to take account of a fault threshold which prevents a too sensitive response to surface changes. In this respect it is particularly advantageous that the fault threshold can be influenced by suitable choice of the arrangement of the light strip receiving devices 14, 14' or also of the intermediate aperture diaphragm 26.

FIG. 7 reproduces the evaluation circuit of the invention with reference to the example of a light conducting rod 15 as was described with reference to FIGS. 4 and 5.

I claim:

1. In optical fault seeking apparatus for seeking faults in a material web having a longitudinal direction, the apparatus comprising: curved guide means having a curved guide surface around which the web is guided to define a convexly curved region of said web, with said convexly curved region having an apex line;

a light scanning device for directing a scanning beam of light onto said material web at said apex line thereby generating a strip-like line of light on said material web at said apex line, wherein said strip-like line of light extends, when said material web is faultfree, transverse to said longitudinal direction along said apex line over said web;

a light receiving device which contains photoelectric converters onto which light emerging from said line of light on said material web is deflected;

and wherein said scanning beam impinges at a shallow angle onto said material web, the improvement wherein said light receiving device is formed by first and second light receivers which each have an associated photoelectric converter, with each of said photoelectric converters comprising at least one photoreceiver, with said first and second light receivers being arranged in the light remitted from the material web at respective angles to a tangent plane to said convexly curved region of said web at said apex line, said first and second light receivers being disposed somewhat outside of an angle corresponding to specular reflection at said material web parallel to said line of light and at a distance from one another such that said first light receiver receives light from a first strip-like region extending close to said curved guide means and parallel to said line of light, and said second light receiver receives light from a second strip-like region removed from said curved guide means and parallel to said line of light, with said first and second strip-like regions being displaced in opposite directions perpendicular to said line of light by a predetermined amount.

2. Fault seeking apparatus in accordance with claim 1, wherein respective first and second electrical signals are generated by first and second photoelectric converters associated with said first and second light receiving devices respectively, and wherein said first and second electrical signals are applied to respective inputs of a differential amplifier forming part of an associated electronic evaluation circuit.

3. Fault seeking apparatus in accordance with claim 1, wherein said material web is a web of translucent material and wherein said strip-like line of light is sufficiently wide that it embraces said material web in the direction of thickness of said material web starting from said curved guide surface and extending at least aoproximately up to the highest raised bump in said web which occurs in practice.

4. Fault seeking apparatus in accordance with claim 1 wherein optical image forming means is disposed between said line of light and said first and second light receivers, parallel to said line of light and images said first and second strip-like regions onto said first and second light receivers respectively.

5. Fault seeking apparatus in accordance with claim 4, wherein said optical image forming means comprises a cylindrical lens.

6. Fault seeking apparatus in accordance with claim 1, wherein said first and second strip-like regions are only displaced in opposite directions perpendicular to said line of light by such an amount that they still clearly overlap the latter when the latter is undistorted.

7. Fault seeking apparatus in accordance with claim 6, wherein said first and second strip-like regions overlap approximately one half of said strip-like line of light.

8. Fault seeking apparatus in accordance with claim 1, wherein said first and second receiving devices comprise spaced apart rows of diodes forming said photoconverters.

9. Fault seeking apparatus in accordance with claim 1, wherein each of said first and second light receiving devices comprises a respective light conducting rod, and wherein each said light conducting rod has a first side surface defining a light inlet on which light received from said line of light falls and a second side surface diametrically opposite to said first side surface, with a strip-like mirror raster extending along said second side surface, and wherein a respective photoreceiver is arranged at at least one end face of each said light conducting rod.

10. Fault seeking apparatus in accordance with claim 1, the apparatus further comprising a roof-like strip mirror extending parallel to said line of light, said roof-like strip mirror having first and second mutually inclined surfaces, a first cylindrical lens disposed between said line of light and said roof-like strip mirror to form an image of said first strip-like region on said first surface of said roof-like strip mirror and an image of said second strip-like region on said second surface of said roof-like strip mirror; second and third cylindrical lenses disposed on respective sides of said roof-like strip mirror; and first and second light conducting rods disposed on respective sides of said roof-like strip mirror, each said light conducting rod having a first side surface defining a light inlet on which light received from said line of light via said roof-like strip mirror falls, and a second side surface diametrically opposite to said first side surface with a strip-like mirror raster extending along said second side surface; wherein said first cylindrical lens concentrates the image of said first strip-like region formed on said first surface of said roof-like strip mirror onto the mirror raster of said first light conducting rod, and wherein said second cylindrical lens concentrates the image of said second strip-like region formed on said second surface of said roof-like strip mirror onto the mirror raster of said second light conducting rod.

11. Fault seeking apparatus in accordance with claim 1, and further comprising a first elongate cylindrical lens disposed parallel to said line of light and spaced therefrom with said first cylindrical lens and said line of light defining an optical axis, a deflecting mirror disposed on one side of said optical axis with said cylindrical lens forming an image of one of said first and second strip-like regions on said deflecting mirror and a further image of the other of said first and second strip-like regions alongside said deflecting mirror on an opposite side of said optical axis; a first light conductng rod forming one of said light receivers and having a light entry surface and a mirror raster disposed diametrically opposite to said light entry surface; a second cylindrical lens disposed between said deflecting mirror and said first light conducting rod to concentrate light deflected at said deflecting mirror and originating from the strip-like region associated with the respective light receiver onto said mirror raster; a second light conducting rod having a further light inlet and a second mirror raster disposed diametrically opposite to said further light inlet; and a third cylindrical lens, wherein light from said further image is concentrated by said third cylindrical lens onto said second mirror raster of said second light conducting rods.

12. Fault seeking apparatus in accordance with claim 1 and further comprising a light conducting rod having first and second end faces, a first side surface defining a light inlet and a second side surface disposed opposite to said first side surface; first and second strip-like mirror rasters disposed at said second surface, wherein said first mirror raster is disposed to receive light from said first strip-like region and to direct it at angles of total internal reflection to a first said photoconverter provided at said first end face, and wherein said second mirror raster is disposed to receive light from said second strip-like region and to direct it at angles of total internal reflection to a second said photoconverter disposed at said second end face.

13. Fault seeking apparatus in accordance with claim 12, wherein a first cylindrical lens is disposed between said light conducting rod and said line of light, wherein said light conducting rod is of substantially circular cross-section and wherein said first cylindrical lens together with said light conducting rod images said first and second strip-like regions onto said first and second mirror rasters respectively.

14. Fault seeking apparatus in accordance with claim 1, wherein said first and second strip-like regions are sufficiently wide that, on the occurrence of faults in said web a deformed line of light results which still largely falls on one of said first and second strip-like regions.

15. Fault seeking apparatus in accordance with claim 1, wherein said curved guide means comprises a roller.

16. Fault seeking apparatus in accordance with claim 15, wherein said roller has an outer periphery which is matt black.

17. Fault seeking apparatus in accordance with claim 1, wherein said shallow angle measured relative to said tangent plane lies in the range from 10° to 30°.

18. Fault seeking apparatus in accordance with claim 17, wherein said shallow angle is approximately 20°.

19. Fault seeking apparatus in accordance with claim 1, wherein a cylindrical lens is provided to form images of said first and second strip-like regions, said line of light and said cylindrical lens defining an optical axis with said optical axis being disposed at an angle in the range from 3° to 7° to said angle of specular reflection outside of said angle of specular reflection.

20. Fault seeking apparatus in accordance with claim 19, wherein said angle lies in the range from 4° to 6°.

21. Fault seeking apparatus in accordance with claim 20, wherein said angle is substantially 5°.

22. Fault seeking apparatus in accordance with claim 20 and further comprising a third light receiver disposed to receive back scattered light from said line of light, said third light receiver subtending an angle in the range from 50° to 70° to said scanning beam.

23. Fault seeking apparatus in accordance with claim 22, wherein said third light receiver subtends an angle of substantially 60° relative to said scanning beam.

24. Fault seeking apparatus in accordance with claim 1 and further comprising a cylindrical lens disposed to form first and second intermediate images of said first and second strip-like regions respectively and a strip-like aperture diaphragm disposed between said first and second intermediate images of said first and second strip-like regions so that only light from said first and second strip-like regions is received by said first and second light receiver.

25. Fault seeking apparatus in accordance with claim 24, wherein said strip-like aperture diaphragm is of adjustable width.

* * * * *